United States Patent
Levis et al.

(10) Patent No.: US 8,529,060 B2
(45) Date of Patent: Sep. 10, 2013

(54) INTRAOCULAR LENS ALIGNMENT USING CORNEAL CENTER

(75) Inventors: Ilias Levis, Westwood, MA (US); Jonathan H. Talamo, Newton, MA (US)

(73) Assignee: Alcon Research, Ltd., Fort Worth, TX (US)

(*) Notice: Subject to any disclaimer, the term of this patent is extended or adjusted under 35 U.S.C. 154(b) by 396 days.

(21) Appl. No.: 12/705,847

(22) Filed: Feb. 15, 2010

(65) Prior Publication Data

US 2010/0208200 A1 Aug. 19, 2010

Related U.S. Application Data

(60) Provisional application No. 61/153,709, filed on Feb. 19, 2009, provisional application No. 61/155,562, filed on Feb. 26, 2009.

(51) Int. Cl.
  *A61B 3/10* (2006.01)
(52) U.S. Cl.
  USPC .......................... 351/204; 351/246
(58) Field of Classification Search
  USPC .............. 351/204, 205, 208, 209, 246
  See application file for complete search history.

(56) References Cited

U.S. PATENT DOCUMENTS

| | | | |
|---|---|---|---|
| 5,089,022 A | 2/1992 | Koester et al. | |
| 5,740,802 A | 4/1998 | Nafis et al. | |
| 5,740,803 A * | 4/1998 | Gray et al. | 600/407 |
| 5,757,461 A | 5/1998 | Kasahara et al. | |
| 5,867,210 A | 2/1999 | Rod | |
| 5,975,084 A | 11/1999 | Alpins | |
| 6,241,356 B1 | 6/2001 | Von Wallfeld et al. | |
| 6,352,519 B1 | 3/2002 | Anis et al. | |
| 7,146,983 B1 | 12/2006 | Hohla et al. | |
| 7,331,667 B2 | 2/2008 | Grotehusmann et al. | |
| 7,654,668 B2 | 2/2010 | Neuhann et al. | |
| 2002/0097378 A1 | 7/2002 | Saito et al. | |
| 2003/0053025 A1 | 3/2003 | Turner et al. | |

(Continued)

FOREIGN PATENT DOCUMENTS

| | | |
|---|---|---|
| EP | 1316287 A2 | 6/2003 |
| RU | 2209053 C2 | 10/2001 |

(Continued)

OTHER PUBLICATIONS

Arbelaez et. al., "Clinical Outcomes of Corneal Vertex Versus Central Pupil References with Aberration-Free Ablation Strategies and LASIK," Dec. 2008, Investigative Ophthalmology & Visual Science, Dec. 2008, Lnkd-Pubmed: 18658090, vol. 49, NR. 12, pp. 5287-5294, XP002584895, ISSN: 1552-5783, Materials and Methods: p. 5287, Figure 5.

(Continued)

*Primary Examiner* — Hung Dang
(74) *Attorney, Agent, or Firm* — Jonathan E. Prejean

(57) ABSTRACT

A method for generating a radial alignment guide for an eye includes collecting preoperative corneal topography data. The data includes a corneal vertex location and a pupil center location for an eye that is not dilated. The method then includes locating a dilated pupil center for the eye after the eye is dilated. The method further includes determining an adjusted offset between the corneal vertex and the dilated pupil center and displaying alignment data on an image of the eye based on the adjusted offset.

23 Claims, 2 Drawing Sheets

(56) References Cited

U.S. PATENT DOCUMENTS

| | | | |
|---|---|---|---|
| 2003/0071893 A1 | 4/2003 | Miller et al. |
| 2003/0120266 A1 | 6/2003 | Fujieda |
| 2004/0100619 A1 | 5/2004 | Olivier et al. |
| 2004/0102799 A1 | 5/2004 | Perez et al. |
| 2005/0025365 A1 | 2/2005 | Oosawa |
| 2005/0117118 A1 | 6/2005 | Miller et al. |
| 2005/0225721 A1 | 10/2005 | Harris et al. |
| 2006/0247659 A1 | 11/2006 | Moeller et al. |
| 2007/0055222 A1 | 3/2007 | Hohla et al. |
| 2008/0247616 A1 | 10/2008 | Pescatore et al. |

FOREIGN PATENT DOCUMENTS

| | | |
|---|---|---|
| RU | 2255716 C1 | 10/2003 |
| WO | WO 92/03989 | 3/1992 |
| WO | WO 01/28476 | 4/2001 |
| WO | WO 01/78584 | 10/2001 |
| WO | WO 01/89373 | 11/2001 |
| WO | WO 02/064031 | 8/2002 |
| WO | WO 02/074248 | 9/2002 |
| WO | WO 03/022137 | 3/2003 |
| WO | WO 2006/044056 | 4/2006 |
| WO | WO 2008/008044 | 1/2008 |

OTHER PUBLICATIONS

Ma, et. al., "Simple Method for Accurate Alignment in Toric Phakic and Aphakic Intraocular Lens Implantation," Journal Cataract and Refractive Surgery, Surgery, Fairfax, VA Lnkd-DOI: 10.10163/J.JCRS.2008.04.041, vol. 34, No. 10, Oct. 1, 2008, pp. 1631-1636, XP025627296, ISSN:0886-3350.

Nguyen, Et. al., "Digital Overlay Technique for Documenting Toric Intraocular Lens Axis Orientation," Oct. 2000, Journal of Cataract and Refractive Surgery, Oct. 2000, Lnkd-PubMed: 11033397, vol. 26, NR. 10, pp. 1496-1504, XP002584785, ISSN: 0886-3350.

Yang, et. al., "Pupil Location Under Mesopic, Photopic, and Pharmacologically Dilated Conditions," Investigative Ophthalmology & Visual Science, Association for Research in Vision and Ophthalmology, US, vol. 43, No. 7, Jul. 1, 2002, pp. 2508-2512, XP002537709, ISSN: 0146-0404, Pupil Center Location; p. 2509-2510, Discussion, p. 2511-2512.

European Search Report for Application No. 08162267.2, Publication No. EP2025305, Published Feb. 18, 2009, 3 pages.

International Search Report for International Application No. PCT/US2010/024482, filed Feb. 17, 2010, Publication No. WO/2010/096492, Published Aug. 26, 1010, dated Jun. 15, 2010, 4 pages.

Written Opinion for International Application No. PCT/US2010/024482, filed Feb. 17, 2010, Publication No. WO/2010/096492, Published Aug. 26, 1010, dated Jun. 15, 2010, 6 pages.

International Search Report for International Application No. PCT/US2010/024483, filed Feb. 17, 2010, Publication No. WO/2010/096493, Published Aug. 26, 1010, dated Jun. 15, 2010, pages.

Written Opinion for International Application No. PCT/US2010/024483, filed Feb. 17, 2010, Publication No. WO/2010/096493, Published Aug. 26, 1010, dated Jun. 15, 2010, 6 pages.

European Search Report for Application No. 11162125.6, Publication No. EP2353546, Published Aug. 10, 2011, dated Jun. 20, 2011, 3 pages.

\* cited by examiner

INTRAOCULAR LENS ALIGNMENT USING CORNEAL CENTER

RELATED APPLICATIONS

This application claims priority under 35 U.S.C. §119(e) to provisional application Ser. No. 61/153,709, filed Feb. 19, 2009, and provisional application Ser. No. 61/155,562, filed Feb. 26, 2009.

BACKGROUND

The rotational orientation of an intraocular lens (IOL) is becoming an increasingly important aspect of modern cataract surgery. While sophisticated algorithms involving automated eye tracking have evolved for monitoring the pupil center and corneal limbus during laser vision correction surgery, each of these require the ability of the eye to actively fixate on a target. This approach may not be available in procedures such as cataract surgery where an anesthetic is typically used, such as a periocular anesthetic injection rendering the eye unable to voluntarily focus or fix on a target. Even when topical anesthesia is utilized, it can be difficult for a patient to maintain fixation and the physiologic pupil cannot be used, as the pupil must remain dilated while the IOL is inserted and rotated into position.

A laser vision correction treatment can be positioned to center over the physiologic pupil. However, for an intraocular lens centered inside the capsular bag of the crystalline lens (which has been removed) or the ciliary sulcus, the center point of the IOL is more closely related to the corneal vertex than the pupil center, because the anatomy of the capsular bag and the ciliary sulcus more closely corresponds to the corneal vertex. If the rotational axis of an IOL is to be based on the pupil center, alignment must be determined with reference to the dilated pupil because the center of an undilated pupil (the pupil centroid) will vary up to 1 mm in a normal eye with constriction or dilation in relation to photic or accommodative stimuli. In contrast, the center of a dilated pupil remains more constant.

SUMMARY

In certain embodiments of the present invention, a method for generating a radial alignment guide for an eye includes collecting preoperative corneal topography data. The data includes a corneal vertex location and a pupil center location for an eye that is not dilated. The method then includes locating a dilated pupil center for the eye after the eye is dilated. The method further includes determining an adjusted offset between the corneal vertex and the dilated pupil center and displaying alignment data on an image of the eye based on the adjusted offset. In particular embodiments, software embodied in a computer-readable medium is executable by a processor to perform the steps of such a method.

In other embodiments, a system for generating a radial alignment guide for an eye includes a memory, a process, and a display. The memory is operable to store preoperative corneal topography data comprising a corneal vertex location and a pupil center location for an eye that is not dilated. The processor is operable to locate a dilated pupil center for the eye after the eye is dilated and determine an adjusted offset between the corneal vertex and the dilated pupil center. The display is operable to display alignment data on an image of the eye based on the adjusted offset.

BRIEF DESCRIPTION OF THE DRAWINGS

The invention may be understood with reference to the following drawings wherein.

DETAILED DESCRIPTION

Figure 1:
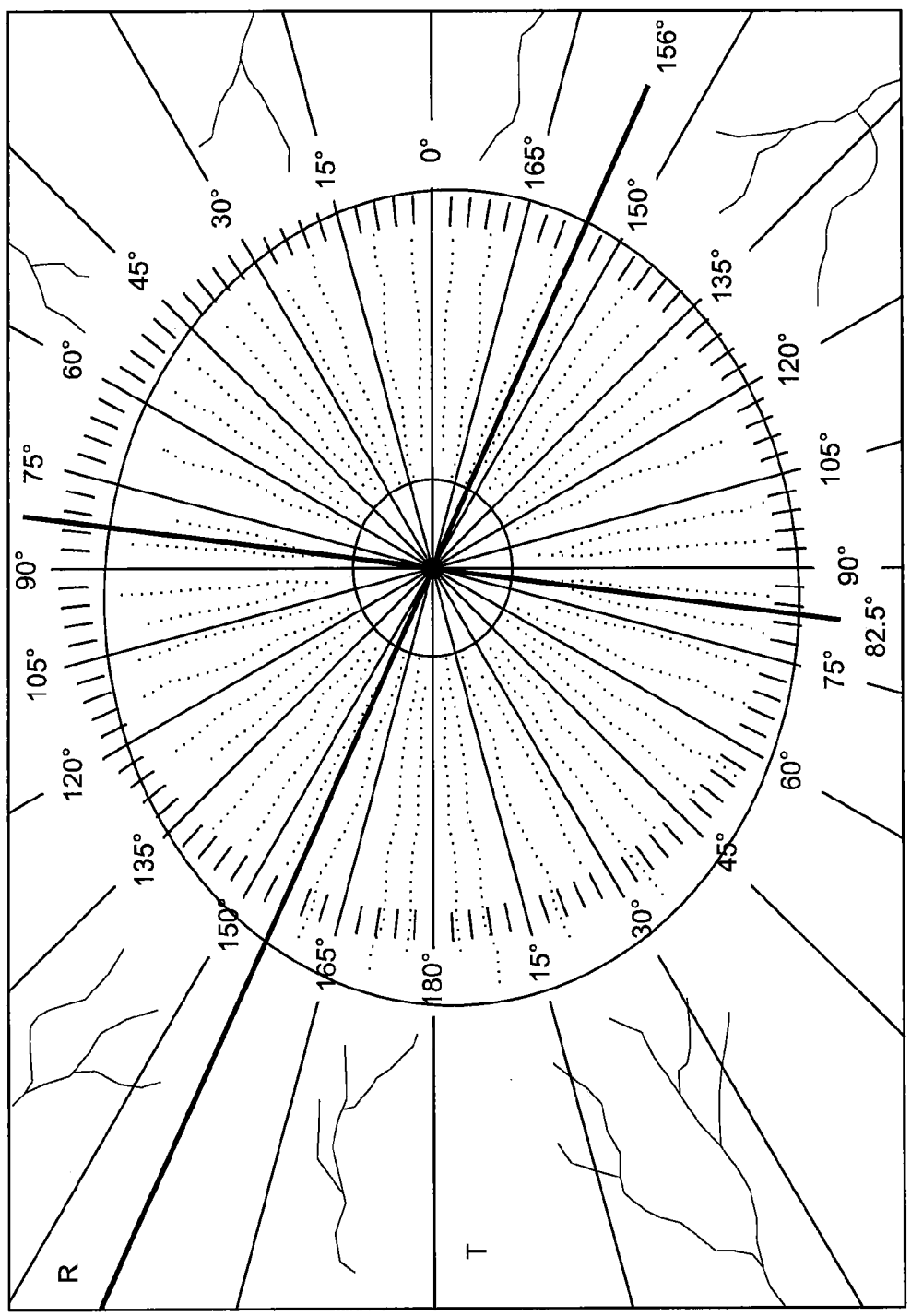
FIG. 1 shows an image of an eye with a radial grid overlay.

Disclosed herein are techniques for determining a location of the corneal vertex and the cyclo-torsional position of the eye in the supine position as it relates to the position of the eye as determined during fixation of the un-anesthetized eye on a target in the seated, upright position. Once the position of the corneal vertex is determined, anatomical landmarks on the iris, sclera, or conjunctival or episcleral tissues of the eyeball may then be used along with the corneal vertex to create two or more reference points, thus allowing reproducible localization of the angle of a specific meridian (in degrees) on the surface of the eye, which may in turn allow for exact rotational positioning of an intraocular lens inside the eye to correct for astigmatism or other asymmetric optical aberrations.

As noted above, the anatomic placement of an intraocular lens (IOL) in the capsular bag or ciliary sulcus is more closely aligned with the corneal vertex. Moreover, IOLs are frequently designed to correct refractive errors, such as aberrations, that result primarily from the corneal shape. The corneal shape is in turn determined with respect to the corneal vertex using, for example, a corneal topographer with patient fixation. For most patients, the visual axis will be aligned with the corneal vertex, so that the resulting measurements will measure the corneal topography relative to the corneal vertex, including any refractive aberrations of the cornea. Even in those cases where the visual axis is at an angle with respect to the corneal vertex (commonly labeled with the angle name "kappa"), so that the patient fixation produces a slight misalignment between the measurements and the corneal vertex, the alignment will still generally be relatively close. Hence, the corneal vertex is a more suitable reference point for determining the proper alignment of the IOL for successful refractive correction, such as determining the correct rotational alignment for correcting astigmatism. Various embodiments of the present invention advantageously allow for more accurate positioning of an IOL by using the corneal vertex as a reference.

Various aspects of particular embodiments of the present invention are now discussed in greater detail. One example of a method according to a particular embodiment of the present invention may be described as a series of steps. In a first step, a full pharmacologic dilation of the pupil may be achieved using topical medications.

In a second step, a subject may be seated upright with the head and chin positioned in a slit lamp microscope or similar device. In this position, corneal topography images and photographs of the anterior segment of the eye may be taken and analyzed using software. In an embodiment, the photographs may be of adequate quality and detail to allow identification of conjunctival, episcleral, or scleral landmarks that are either part of the ocular anatomy or are placed by a surgeon or other health care provider.

In a third step, a corneal topographic image may be analyzed using commercially available topographer software, and a position of the corneal vertex in relation to the center of the dilated pupil may be determined. The appropriate x,y offset may then be applied to imaging software that creates a radial grid overlay (e.g., 360 degrees) onto the eye or images thereof using the corneal vertex as the centration point for the grid.

In a fourth step, the appropriate axis for rotational placement of an intraocular lens may be determined from anatomic landmarks and a position of the grid, which is superimposed over the view of the eye, e.g., through an operating microscope when the eye is dilated and the patient is in a supine position during surgery.

In a particular embodiment, the pupil diameter may be measured at each step (or several steps, or between steps, or in some other recurring manner) in order to ensure that it remains relatively constant throughout the procedure, thus providing more accurate measurements throughout.

In general, the relationship between eye topography, as obtained utilizing a topographer or similar software, and the pupil center may vary when the pupil is dilated. Thus, for example, in one patient there might be 0.55 mm of horizontal and 0.11 mm vertical distance between the pupil and cornea centers when the pupil is not dilated. In a similar patient, there could be an offset including approximately 0.57 mm of horizontal distance between the pupil and cornea centers but almost no vertical offset when the eye is dilated. Hence, even with pupil centration, it may be necessary to realign the measured topography to the pupil in order to accurately map the topography to the center of the pupil.

In general, basic analytic geometry principles dictate that if we wish to move the pole of a polar coordinate system from (0,0) to $(r_0, theta_0)$, and keep the new polar axis parallel to the old one then we get the following equations relating the new coordinates (r',theta') to the old:

$$r'=sqrt(r^2+r_0^2+2rr_0 \cos(theta-theta_0)),$$

$$theta'=arctan([r \sin(theta)+r_0 \sin(theta_0)]/[r \cos(theta)+r_0 \cos(theta_0)]),$$

$$x=r \cos(theta),$$

$$y=r \sin(theta),$$

$$r=\pm sqrt(x^2+y^2),$$

$$theta=arctan(y/x).$$

In this case, we may assume that (r,theta) are the coordinates of a landmark point on the patient's eye according to a polar coordinate system with origin on the pupil center. The pupil center can be located using a variety of image analysis techniques, including but not limited to the techniques described in U.S. Pat. No. 5,740,803 to Gray et al., which is incorporated herein by reference. The ordered pair $(r_0, theta_0)$ is the coordinates of the cornea center relative to the pupil center as calculated by the topographer and (r',theta') are the new coordinates of the landmark point according to a coordinate system with origin on the cornea center.

In one example, an error calculation characterizing an angular value error when a landmark point is measured in reference to a pupil center as opposed to the cornea center. Specifically, a distance between the pupil and cornea centers of approximately 0.5 mm horizontally causes approximately 9° error in the angular value of the landmark point. An error of this magnitude in rotational alignment of an IOL with asymmetric optics to correct astigmatism or optical aberration is detrimental to the correction effectiveness of the IOL implant considering that every 1° of error introduces 3% astigmatic under correction.

FIG. 1 shows an eye image with a radial grid overlay. The overlay may be centered, for example, on the pupil or on the corneal vertex. The process described above may be used with a system that automatically locates the center of the pupil to re-assign a new coordinate system origin according to the topographer readings and then overlay a 360 degree grid onto an image of an eye using the corneal vertex (as determined above) as the centration point for the grid. Stated differently, an automatic pupil-centered system may be improved using the techniques described herein to capture an offset from the pupil centering to the corneal vertex that may be applied to center the radial grid overlay on the corneal vertex based upon a pupil center that is located within an image of an eye. This system may be usefully employed, for example, to provide a surgical guide or placement and/or orientation of a toric intraocular lens or other orientation-sensitive optical implant. Suitable adaptations to such a system to offset from the pupil center to the corneal vertex will be readily appreciated by one of ordinary skill in the art, and all such variations or modifications are intended to fall within the scope of this disclosure.

Figure 2:
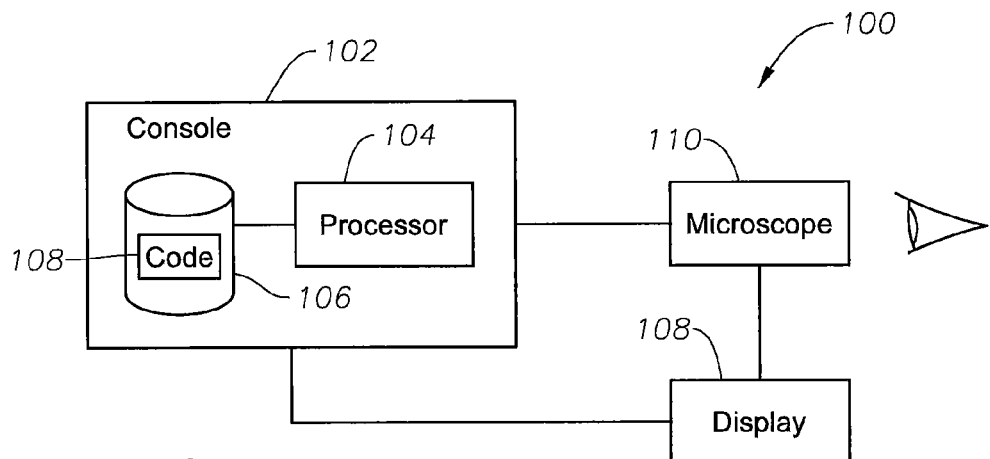
FIG. 2 shows a block diagram of a surgical system according to a particular embodiment of the present invention.

The methods or processes described above, and steps thereof, may be realized in hardware, software, or any combination of these suitable for a particular application. The hardware may include a general-purpose computer and/or dedicated computing device. FIG. 2 is a block diagram of a system 100 for generating a surgical display according to a particular embodiment of the present invention. The system 100 includes a console 102 having a processor 104. The processor 104 may be one or more microprocessors, microcontrollers, embedded microcontrollers, programmable digital signal processors or other programmable device, along with internal and/or external memory 106. The processor 104 may also, or instead, be embodied in an application specific integrated circuit, a programmable gate array, programmable array logic, or any other device or combination of devices that may be configured to process electronic signals. The memory 106 may be any suitable form of data storage, including electronic, magnetic, or optical memory, whether volatile or non-volatile, that includes code 108 comprising instructions executed by processor 104. It will further be appreciated that computer executable code 108 may be created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software.

In the embodiment depicted in FIG. 2, the system 100 also includes a display 108 and a microscope 110 for observing an eye during surgery. The display 108 may include any suitable output device for generating an alignment guide for the eye, including a printer, a video display, or a light projector. In particular embodiments, the display 108 may be coupled to the microscope 110 so that the image is projected into the view of the microscope. The microscope 110 may be any suitable tool for visually inspecting the eye, which may include electronic and/or optical views.

Figure 3:
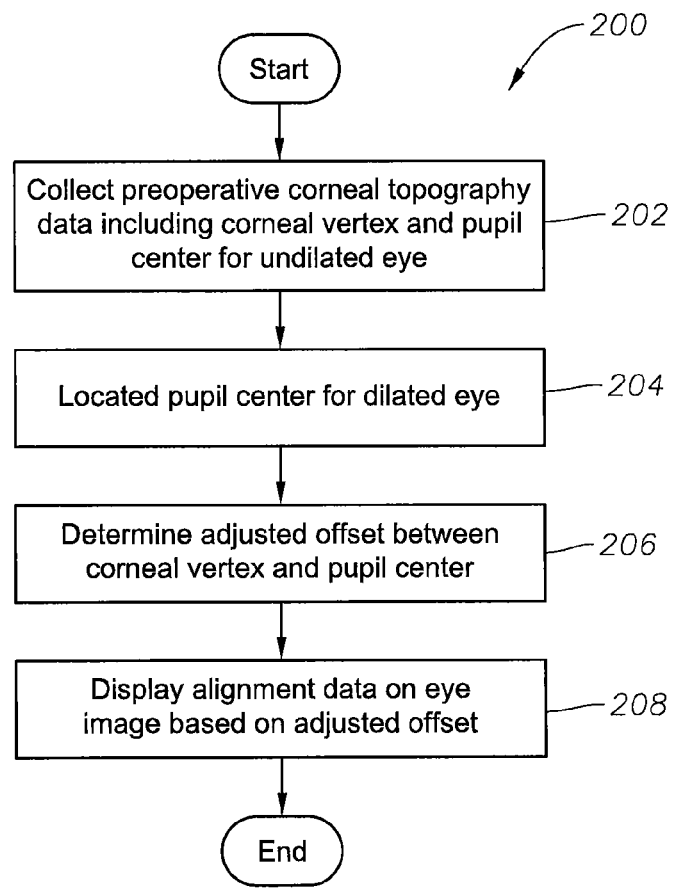
FIG. 3 shows an example method of generating a surgical display according to a particular embodiment of the present invention.

FIG. 3 is a flow chart 200 illustrating an example method for generating a radial alignment guide for an eye. At step 202, preoperative corneal topography data comprising a corneal vertex location and a pupil center location is collected for an eye that is not dilated. At step 204, a dilated pupil center is located for the eye after the eye is dilated. At step 206, an adjusted offset between the corneal vertex and the dilated pupil center. At step 208, alignment data is displayed on an image of the eye based on the adjusted offset.

Thus, in one aspect, each method described above and combinations thereof may be embodied in computer executable code that, when executing on one or more computing devices, performs the steps thereof. In another aspect, the methods may be embodied in systems that perform the steps thereof, and may be distributed across devices in a number of ways, or all of the functionality may be integrated into a dedicated, standalone device or other hardware. In another aspect, means for performing the steps associated with the processes described above may include any of the hardware and/or software described above. All such permutations and combinations are intended to fall within the scope of the present disclosure.

While the invention has been disclosed in connection with the preferred embodiments shown and described in detail, various modifications and improvements thereon will become readily apparent to those skilled in the art.

What is claimed is:

1. A method for generating an alignment alignment guide for surgeon to assist in intraocular lens placement in an eye, comprising:
   collecting preoperative corneal topography data comprising a corneal vertex location and a pupil center location for an eye that is not dilated;
   determining an offset between the corneal vertex location and the pupil center location;
   determining alignment data for an intraocular lens based on the offset;
   locating a dilated pupil center for an image of the eye taken by a camera after the eye is dilated using image analysis software;
   determining an adjusted offset between the corneal vertex and the dilated pupil center; and
   displaying adjusted alignment data on the image of the eye based on the adjusted offset.

2. The method of claim 1, wherein displaying the alignment data comprises displaying a radial grid.

3. The method of claim 1, wherein displaying the alignment data comprises displaying at least one meridian relative to the eye.

4. The method of claim 3, further comprising aligning a protractor relative to the meridian.

5. The method of claim 1, wherein displaying the alignment data further comprises displaying a radial grid.

6. The method of claim 1, wherein locating the pupil center comprises manually moving a pointing device to locate a center of an eye.

7. The method of claim 1, wherein locating the pupil center comprises automatically locating the pupil center using image analysis software.

8. The method of claim 1, wherein displaying the alignment data comprises displaying a cylindrical axis for a toric intraocular lens.

9. A system for generating an alignment guide for a surgeon to assist in intraocular lens placement in an eye, comprising:
   a memory operable to store preoperative corneal topography data comprising a corneal vertex location and a pupil center location for an eye that is not dilated, an offset between the corneal vertex location and the pupil center location, and preoperative alignment data for an intraocular lens based on the offset;
   a processor operable to locate a dilated pupil center for an image of the eye taken by a camera after the eye is dilated and determine an adjusted offset between the corneal vertex and the dilated pupil center; and
   a display operable to display adjusted alignment data on the image of the eye based on the adjusted offset.

10. The system of claim 9, wherein the display of the alignment data comprises a radial grid.

11. The system of claim 9, wherein the display of the alignment data includes a display of at least one meridian relative to the eye.

12. The system of claim 9, further comprising a protractor configured to be aligned relative to the meridian.

13. The system of claim 9, wherein the display of the alignment data comprises a radial grid.

14. The system of claim 9, further comprising a pointing device that is manually movable to indicate a center of the pupil to the processor.

15. The system of claim 9, wherein the processor is operable to locate the pupil center using image analysis software.

16. The system of claim 9, wherein the display of the alignment data comprises a cylindrical axis for a toric intraocular lens.

17. Software embodied in a computer-readable medium executable by a processor to perform the steps of:
   collecting preoperative corneal topography data comprising a corneal vertex location and a pupil center location for an eye that is not dilated, an offset between the corneal vertex location and the pupil center location, and preoperative alignment data for an intraocular lens based on the offset;
   locating a dilated pupil center for an image of the eye taken by a camera after the eye is dilated;
   determining an adjusted offset between the corneal vertex and the dilated pupil center; and
   displaying adjusted alignment data on the image of the eye based on the adjusted offset.

18. The software of claim 17, wherein displaying the alignment data comprises displaying a radial grid.

19. The software of claim 17, wherein displaying the alignment data comprises displaying at least one meridian relative to the eye.

20. The software of claim 17, wherein displaying the alignment data further comprises displaying a radial grid.

21. The software of claim 17, wherein locating the pupil center comprises receiving an indication of the center of the pupil from a pointing device.

22. The software of claim 17, wherein locating the pupil center comprises automatically locating the pupil center using image analysis software.

23. The software of claim 17, wherein displaying the alignment data comprises displaying a cylindrical axis for a toric intraocular lens.

* * * * *